(12) United States Patent
Leirs et al.

(10) Patent No.: US 12,730,105 B2
(45) Date of Patent: Sep. 8, 2026

(54) METHOD FOR DROPLET LOADING INTO NANOWELLS

(71) Applicants: Abbott Laboratories, Abbott Park, IL (US); Katholieke Universiteit Leuven KU Leuven Research & Development, Leuven (BE)

(72) Inventors: Karen Leirs, Leuven (BE); Elena Pérez-Ruiz, Leuven (BE); Jeroen Lammertyn, Leuven (BE)

(73) Assignee: Abbott Laboratories, Abbott Park, IL (US)

( * ) Notice: Subject to any disclaimer, the term of this patent is extended or adjusted under 35 U.S.C. 154(b) by 1020 days.

(21) Appl. No.: 17/909,110

(22) PCT Filed: Mar. 9, 2021

(86) PCT No.: PCT/US2021/021502

§ 371 (c)(1),
(2) Date: Sep. 2, 2022

(87) PCT Pub. No.: WO2021/183512

PCT Pub. Date: Sep. 16, 2021

(65) Prior Publication Data

US 2023/0096625 A1 Mar. 30, 2023

Related U.S. Application Data

(60) Provisional application No. 62/987,639, filed on Mar. 10, 2020.

(51) Int. Cl.
*B01L 3/00* (2006.01)
*G01N 33/543* (2006.01)

(52) U.S. Cl.
CPC .. *G01N 33/54386* (2013.01); *B01L 3/502761* (2013.01); *B01L 2200/0642* (2013.01);
(Continued)

(58) Field of Classification Search
None
See application file for complete search history.

(56) References Cited

U.S. PATENT DOCUMENTS

2009/0263834 A1* 10/2009 Sista ................ G01N 33/54333
435/7.9
2018/0104694 A1* 4/2018 Huff .................. G01N 33/5302

FOREIGN PATENT DOCUMENTS

CN 110621405 A 12/2019
WO 2016161400 A1 10/2016
WO 2018136509 A1 7/2018

OTHER PUBLICATIONS

Brinkworth et al., "Selected non-ionic biological detergents enhance signal intensity of intact bovine serum albumin by matrix-assisted laser desorption/ionisation time-of-flight mass spectrometry", Eur. J. Mass Spectrom, 13, pp. 311-319, published Nov. 9, 2007. (Year: 2007).*

(Continued)

*Primary Examiner* — Rebecca M Giere
(74) *Attorney, Agent, or Firm* — Lisa Mueller; Casmir Jones SC

(57) ABSTRACT

Provided herein is a method of loading wells with a liquid droplet, or a portion thereof, wherein each liquid droplet comprises solid supports and a detergent or surfactant, such that the detergent or surfactant reduces the contact angle between the liquid droplet and the wells. Also provided is a method of detecting and quantifying an analyte of interest in a sample, which involves loading wells in an array with a liquid droplet according to aforementioned method, wherein the liquid droplet comprises an analyte captured on a solid support.

17 Claims, 5 Drawing Sheets

Tween 80

(52) U.S. Cl.
CPC ... *B01L 2200/0647* (2013.01); *B01L 2200/16* (2013.01); *B01L 2300/0636* (2013.01); *B01L 2300/0645* (2013.01); *B01L 2300/0893* (2013.01); *B01L 2300/161* (2013.01)

(56) References Cited

OTHER PUBLICATIONS

Wenqian Feng et al: "Droplet Microarrays: From Surface Patterning to High-Throughput Applications", Advanced Materials, vol. 30, No. 20, May 1, 2018 (May 1, 2018), p. 1706111, XP055588875.

Erica Ueda et al: "DropletMicroarray: facile formation of arrays of microdroplets and hydrogel micropads for cell screening applications", Lab On a Chip, Jan. 1, 2012 (Jan. 1, 2012), XP055043855.

* cited by examiner

Pluronic F68

Tetronic 90R4

Tween 20

Tween 80

FIG. 5A

FIG. 5B corner center

Triton X100

METHOD FOR DROPLET LOADING INTO NANOWELLS

CROSS REFERENCE TO RELATED APPLICATIONS

This application is a national stage application of PCT/US2021/021502 filed Mar. 9, 2021, which claims the benefit of U.S. Provisional Patent Application No. 62/987,639, filed Mar. 10, 2020, which is incorporated by reference herein, each of which are hereby incorporated by reference in their entirety.

BACKGROUND OF THE INVENTION

The ability to detect low concentrations of protein biomarkers can differentiate healthy and disease states at a much earlier stage, as well as monitor disease progression, and is therefore critical for improving diagnostic tools. Detection of single molecules in femtoliter sized wells is a promising approach for identifying new diagnostic protein markers at ultrasensitive concentrations. In bead-based digital assays, target protein biomarkers can be digitally detected through confinement of single targets in a nanowell array using magnetic beads, and the captured target molecules can be detected via enzymes that produce a fluorescent signal. Digital microfluidics (DMF) is a promising technology that involves the manipulation of small discrete droplets on a two-dimensional surface and has been used to shuttle droplets of suspended beads for loading into nanowell arrays. However, one of the challenges to bead based digital assays is efficient loading of single beads into the femtoliter sized chambers.

There remains a need for improved methods for loading droplets containing suspended beads into nanowell arrays. The present disclosure provides such methods.

BRIEF SUMMARY OF THE INVENTION

The disclosure provides a method of loading wells with liquid droplets, which method comprises: (a) contacting an array of wells with a liquid droplet, wherein (i) one or more wells of the array is of sufficient size to have loaded therein a portion of the liquid droplet, and (ii) each portion of the liquid droplet comprises a solid support and a detergent or surfactant, (b) moving the liquid droplet over the array of wells, wherein the detergent or surfactant reduces the contact angle between the liquid droplet and the wells, and whereby a portion of the liquid droplet is loaded into each well of the array; (c) removing any portion of the liquid droplet that is not loaded into wells from the surface of the array; and (d) sealing the loaded wells.

The disclosure also provides a method of detecting and quantifying an analyte of interest in a sample, which method comprises (a) providing a first liquid droplet containing an analyte of interest; (b) providing a second liquid droplet containing a solid support which comprises a first binding member that specifically binds to the analyte of interest; wherein either the first liquid droplet or the second liquid droplet further comprises a detergent or surfactant; (c) using energy to exert a force to manipulate the first liquid droplet and the second liquid droplet to create a droplet mixture comprising one or more liquid droplets each of which comprises analyte of interest captured on the surface of the solid support; (d) loading wells in an array with the one or more liquid droplets according to the methods described herein; and (e) detecting and quantifying the analyte of interest.

BRIEF DESCRIPTION OF THE DRAWING(S)

FIGS. 5A and 5B are images of the corner (FIG. 5A) and center (FIG. 5B) of a nanowell plate loaded with droplets comprising the detergent Triton X 100.

DETAILED DESCRIPTION OF THE INVENTION

Figures 1A, 1B:
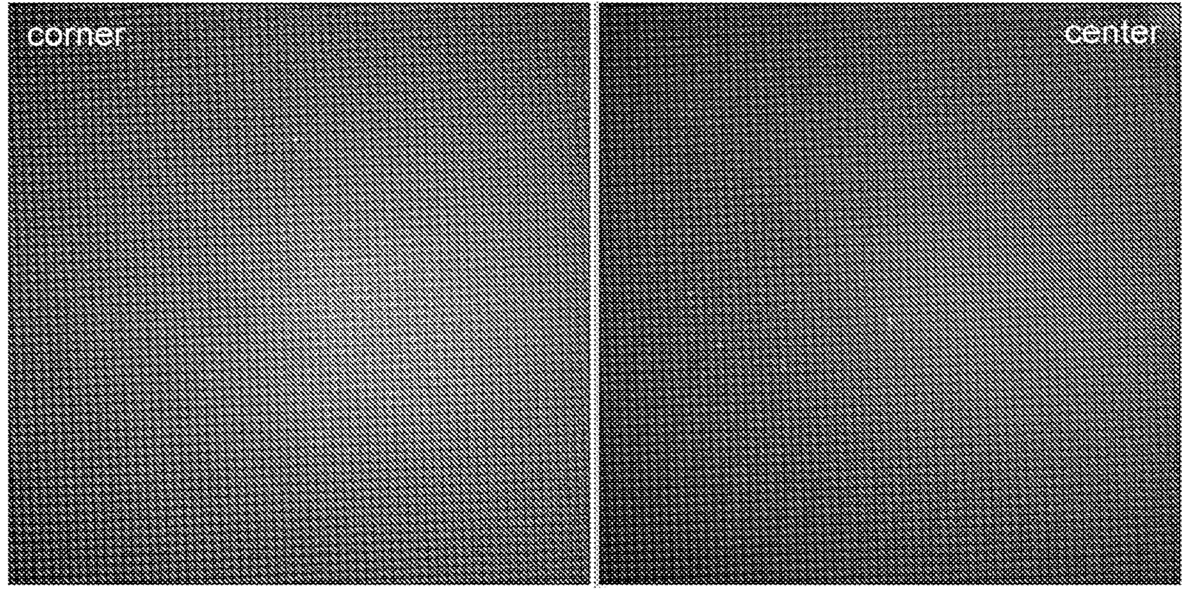
FIGS. 1A and 1B are images of the corner (FIG. 1A) and center (FIG. 1B) of a nanowell plate loaded with droplets comprising the detergent Pluronic F68.

The present disclosure is predicated, at least in part, on the discovery that the addition of a surfactant or detergent to a liquid droplet containing microparticles in single molecule detection methods improves loading of the droplet onto nanowell arrays. It is believed that the use of a surfactant in accordance with the methods described herein confers a hydrophilic appearance on the surface of droplets, making it easier to wet wells of an array. The presence of the surfactant or detergent also relieves the trapped air in the "Cassie State," which describes the effective contact angle θc for a liquid on a composite surface (Cassie, A. B. D. and Baxter, S., *Transactions of the Faraday Society,* 40: 546 (1944)). The surfactant or detergent reduces the contact angle of the droplet and the nanowell, resulting in more efficient droplet loading and wetting of wells. Thus, the disclosure provides methods of loading wells with a liquid droplet, or portions thereof, wherein the liquid droplet or portion thereof comprises a solid support and a detergent or surfactant.

Also provided herein are methods for measuring or detecting an analyte of interest present in a biological sample. In such methods, a sample droplet containing the target analyte of interest may be merged with a droplet containing beads (such as magnetic beads) on which a first specific binding member that specifically binds to the target analyte of interest present in the sample is attached. Merging creates a single droplet which may be incubated for a time sufficient to allow binding of the first specific binding member to an analyte of interest present in the sample droplet. Optionally, the single droplet may be agitated to facilitate mixing of the sample with the first specific binding member. Mixing may be achieved by moving the single droplet back and forth, moving the single droplet around over a plurality of electrodes, splitting a droplet and then merging the droplets, or using SAWs, and the like. Next, the single droplet may be subjected to a magnetic force to retain the beads at a location in the device while the droplet may be moved away to a waste chamber or pad and replaced with a droplet containing a second binding member. The second specific binding member may be detectably labeled. The label may be any label that can be optically detected. For example, the label may be a fluorescent label. An optional wash step may be performed, prior to adding the second binding member, by moving a droplet of wash buffer to the location at which the beads are retained using the force, e.g., magnetic. The beads may or may not be resuspended in the wash buffer. If magnetic beads are used, a magnetic force can be applied to the magnetic beads and the wash buffer is transported to a waste location. After a period of time sufficient for the second specific binding member to bind the analyte of interest bound to the first binding member, the droplet containing the second specific binding member may be moved away while the beads are retained at the location. The beads may be washed using a droplet of wash buffer. Following the wash step, a droplet containing the labeled beads which has a complex of the first binding member, analyte of interest and the second binding member may be moved over to the detection module (such as by removal of the magnetic force if magnetic beads are used). As explained herein, the immunoassay may be carried out in the sample preparation module. The labeled beads may be allowed to settle into the array of wells in the detection module. The beads may settle using gravitational force or by applying electric or magnetic force. Following a wash step to remove any beads not located inside the wells, the wells may be sealed by using a hydrophobic liquid.

Liquid Droplets

The methods described herein involve contacting an array of wells with a liquid droplet, wherein one or more portions of the liquid droplet settle into the wells of the array, each of which portion comprises a solid support and a detergent or surfactant. In other words, upon contact with the array of wells, the liquid droplet is moved over the array of wells, and one or more portions of the droplet (e.g., 1, 50, 100, 500, 1,000, 5,000, 10,000, 25,000, 50,000, 75,000, 100,000, 200,000, 300,000, 400,000, 500,000 or more portions), are loaded into the wells. The terms "droplet," "liquid droplet," and "fluidic droplet" are used interchangeably herein to refer to a discrete volume of liquid that is roughly spherical in shape and is bounded on at least one side by a wall or substrate (e.g., a solid support). "Roughly spherical" in the context of the droplet refers to shapes such as spherical, partially flattened sphere, e.g., disc shaped, slug shaped, truncated sphere, ellipsoid, hemispherical, or ovoid. The volume of the liquid droplets disclosed herein may range from about 10 µl to about 5 µL, about 10 µl-1 µL, about 7.5 µl-10 µL, about 5 µl-1 nL, about 2.5 µl-10 nL, about 1 µl-100 nL, or a range defined by any two of the foregoing values. For example, the volume of a liquid droplet may be 10 µl or less (e.g., 5 µl, 1 µl, 800 nL, 500 nL, or less).

In certain embodiments, a liquid droplet is comprised of aqueous liquid, an immiscible liquid, or a polarizable liquid. In other embodiments, the liquid droplet is a hydrophobic liquid droplet. In other embodiments, the liquid droplet is a hydrophilic liquid droplet.

Droplets may be formed using surface tension properties of the liquid. Actuation of a droplet may be based on the presence of electrostatic forces generated by electrodes placed beneath the bottom surface on which the droplet is located. Different types of electrostatic forces can be used to control the shape and motion of the droplets. One technique that can be used to create the foregoing electrostatic forces is based on dielectrophoresis, which relies on the difference of electrical permittivities between the droplet and surrounding medium and may utilize high-frequency alternating current (AC) electric fields. Another technique that can be used to create the foregoing electrostatic forces is based on electrowetting, which relies on the dependence of surface tension between a liquid droplet present on a surface and the surface on the electric field applied to the surface.

One or more solid supports, such as a bead or microparticle as described herein, may be encapsulated in a liquid droplet, or a portion thereof, using any suitable method or microfluidics device known in the art. Such methods and devices are disclosed in, for example, International Patent Application Publications WO 2016/161400 and WO 2016/161402; U.S. Pat. Nos. 9,625,454 and 9,675,972; Kim et al., *Scientific Reports,* 7: Article number: 46260 (2017); Guan et al., *Biomicrofluidics,* 8(1): 014110 (2014); Witters et al., *Lab Chip,* 13(11): 2047-54 (2013); Decrop et al., *Anal. Chem.,* 88: 8596-8603 (2015); and Kaminski T. S. and P. Garstecki, *Chem Soc Rev.,* 46(20): 6210-6226 (2017).

In addition to a solid support, the liquid droplet, and each portion thereof, further comprises a surfactant or a detergent. As discussed above, the presence of a surfactant or detergent improves loading of bead-containing liquid droplets into nanowell arrays using digital microfluidics. While surfactants have been used in digital microfluidics platforms to induce droplet movement across an array, the present disclosure is the first to demonstrate that incorporation of surfactants into droplets themselves improves bead loading efficiency. Indeed, the disclosed method allows for improved loading of portions of the liquid droplet onto wells as compared to liquid droplets that lack a detergent or surfactant. The term "surfactant," as used herein, refers to a compound that lowers the surface tension (or interfacial tension) between two liquids, between a gas and a liquid, or between a liquid and a solid. The term "detergent," as used herein, refers to a surfactant or a mixture of surfactants with cleaning properties in dilute solutions. Any suitable surfactant or detergent may be added to the liquid droplet. Examples of suitable surfactants include anionic surfactants (e.g., anionic sulfate, sulfonate, and phosphate esters), cationic surfactants (e.g., quaternary ammonium salts), zwitterionic surfactants (e.g., phosphatidylserine, phosphatidylethanolamine, phosphatidylcholine, and sphingomyelins), and nonionic surfactants (e.g., ethoxylates, glycerol fatty acid esters, and sorbital fatty acid esters). In one embodiment, the surfactant is the alkylphenol ethoxylate TRITON™ X-100 (available from sources such as Sigma-Aldrich, St. Louis, MO, and Dow Chemical (Midland, MI)). Examples of suitable detergents include, but are not limited to, anionic detergents (e.g. alkylbenzenesulfonates), cationic detergents (e.g., quaternary ammonium salts), and nonionic detergents (e.g., ethoxylates or glycosides). In one embodiment, the detergent is the nonionic detergent TWEEN-20 or TWEEN-80.

The surfactant or detergent may be added to a liquid droplet in any suitable amount or concentration.

Solid Support

Any solid support known in the art can be used in the methods described herein, including but not limited to, solid supports made out of polymeric materials in the form of planar substrates or beads, and the like. For example, the solid support may be a bead, e.g., latex, agarose, sepharose, streptavidin, tosylactivated, epoxy, polystyrene, amino bead, amine bead, carboxyl bead, or the like. In certain embodiments, the bead may be a particle, e.g., a microparticle. The terms "bead" and "particle" are used herein interchangeably and refer to a substantially spherical solid support. The terms "microparticle" and "microbead" are used interchangeably herein and refer to a microbead or microparticle that is allowed to occupy or settle in an array of wells, such as, for example, in an array of wells in a detection module. The microparticle or microbead may contain at least one specific binding member that binds to an analyte of interest and at least one detectable label. Alternatively, the microparticle or microbead may containing a first specific binding member that binds to the analyte and a second specific binding member that also binds to the analyte and contains at least one detectable label.

In some embodiments, the microparticle may be between about 0.1 nm and about 10 microns, between about 50 nm and about 5 microns, between about 100 nm and about 1 micron, between about 0.1 nm and about 700 nm, between about 500 nm and about 10 microns, between about 500 nm and about 5 microns, between about 500 nm and about 3 microns, between about 100 nm and 700 nm, or between about 500 nm and 700 nm. For example, the microparticle may be about 4-6 microns, about 2-3 microns, or about 0.5-1.5 microns. Particles less than about 500 nm may be referred to as "nanoparticles." Thus, the microparticle optionally may be a nanoparticle between about 0.1 nm and about 500 nm, between about 10 nm and about 500 nm, between about 50 nm and about 500 nm, between about 100 nm and about 500 nm, about 100 nm, about 150 nm, about 200 nm, about 250 nm, about 300 nm, about 350 nm, about 400 nm, about 450 nm, or about 500 nm.

In certain embodiments, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, NiO/Fe. Examples of ferrimagnetic materials include $NiFe_2O_4$, $CoFe_2O_4$, $Fe_3O_4$ (or $FeO{\cdot}Fe_2O_3$). Beads can have a solid core portion that is magnetic and is surrounded by one or more non-magnetic layers. Alternately, the magnetic portion can be a layer around a non-magnetic core. The solid support on which a binding member is immobilized may be stored in dry form or in a liquid. The magnetic beads may be subjected to a magnetic field prior to or after contacting with the sample with a magnetic bead on which a binding member is immobilized.

Analyte of Interest

In some embodiments, the solid support comprises an analyte of interest captured on the surface thereof. The terms "analyte," "target analyte," and "analyte of interest," are used interchangeably herein and refer to the analyte being measured in the methods disclosed herein. As will be appreciated by those in the art, any analyte that can be specifically bound by a binding member (e.g., a first specific binding member and a second specific binding member) may be detected and, optionally, quantified using the methods of the present disclosure.

In some embodiments, the analyte may be a biomolecule. Non-limiting examples of biomolecules include macromolecules such as, proteins, lipids, and carbohydrates. In certain instances, analytes include hormones, antibodies, growth factors, cytokines, enzymes, receptors (e.g., neural, hormonal, nutrient, and cell surface receptors) or their ligands, cancer markers (e.g., PSA, TNF-alpha), markers of myocardial infarction (e.g., troponin, creatine kinase, and the like), toxins, drugs (e.g., drugs of addiction), metabolic agents (e.g., including vitamins), and the like. Non-limiting embodiments of protein analytes include peptides, polypeptides, protein fragments, protein complexes, fusion proteins, recombinant proteins, phosphoproteins, glycoproteins, lipoproteins, or the like.

In certain embodiments, the analyte may be a post-translationally modified protein (e.g., phosphorylated, methylated, glycosylated protein) and a corresponding binding member (described below) may be an antibody specific to a post-translational modification. A modified protein may be bound to a first binding member immobilized on a solid support where the first binding member binds to the modified protein but not the unmodified protein. In other embodiments, a first binding member may bind to both the unmodified and the modified protein, and a second binding member may be specific to the post-translationally modified protein.

In some embodiments, the analyte may be a cell, such as, for example, a circulating tumor cell, pathogenic bacteria cell, or a fungal cell. In other embodiments, the analyte may be a virus (e.g., retrovirus, herpesvirus, adenovirus, lentivirus, Filovirus (Ebola), hepatitis virus (e.g., A, B, C, D, and E), or human papilloma virus (HPV)).

A non-limiting list of analytes that may be analyzed by the methods disclosed herein include Aβ42 amyloid beta-protein, fetuin-A, tau, secretogranin II, prion protein, alpha-synuclein, tau protein, neurofilament light chain, parkin, PTEN induced putative kinase 1, DJ-1, leucine-rich repeat kinase 2, mutated ATP13A2, Apo H, ceruloplasmin, peroxisome proliferator-activated receptor gamma coactivator-1 alpha (PGC-1α), transthyretin, vitamin D-binding protein, proapoptotic kinase R (PKR) and its phosphorylated PKR (pPKR), CXCL13, IL-12p40, CXCL13, IL-8, Dkk-3 (semen), p14 endocan fragment, serum, ACE2, autoantibody to CD25, hTERT, CA125 (MUC 16), VEGF, sIL-2, osteopontin, human epididymis protein 4 (HE4), alpha-fetoprotein, albumin, albuminuria, microalbuminuria, neutrophil gelatinase-associated lipocalin (NGAL), interleukin 18 (IL-18), kidney injury molecule-1 (KIM-1), liver fatty acid binding protein (L-FABP), LMP1, BARFI, IL-8, carcinoembryonic antigen (CEA), BRAF, CCNI, EGRF, FGF19, FRS2, GREB1, LZTS1, alpha-amylase, carcinoembryonic antigen (CEA), CA125, interleukin-8 (IL-8), thioredoxin, beta-2 microglobulin, tumor necrosis factor-alpha receptors, CA15-3, follicle-stimulating hormone (FSH), leutinizing hormone (LH), T-cell lymphoma invasion and metastasis 1 (TIAM1), N-cadherin, EC39, amphiregulin, dUTPase, secretory gelsolin (pGSN), PSA (prostate specific antigen), thymosin 015, insulin, plasma C-peptide, glycosylated hemoglobin (HBA1c), C-Reactive Protein (CRP), interleukin-6 (IL-6), ARHGDIB (Rho GDP-dissociation inhibitor 2), CFL1 (cofilin-1), PFN1 (profilin-1), GSTP1 (glutathione S-transferaseP), S100A11 (protein S100-A11), PRDX6 (peroxiredoxin-6), HSPE1 (10 kDa heat shock protein, mitochondrial), LYZ (lysozyme C precursor), GPI (glucose-6-phosphate isomerase), HIST2H2AA (histone H2A type 2-A), GAPDH (glyceraldehyde-3-phosphate dehydrogenase), HSPG2 (basement membrane-specific heparan sulfate proteoglycan core protein precursor), LGALS3BP (galectin-3-binding protein precursor), CTSD (cathepsin D precursor), APOE (apolipoprotein E precursor), IQGAP1 (Ras GTPase-activating-like protein IQGAP1), CP (Ceruloplasmin precursor), and IGLC2 (IGLC1 protein), PCDGF/GP88, EGFR, HER2, MUC4, IGF-IR, p27(kip1), Akt, HER3, HER4, PTEN, PIK3CA, SHIP, Grb2, Gab2, PDK-1 (3-phosphoinositide dependent protein kinase-1), TSC1, TSC2, mTOR, MIG-6 (ERBB receptor feedback inhibitor 1), S6K, src, KRAS, MEK mitogen-activated protein kinase 1, cMYC, TOPO U topoisomerase (DNA) U alpha 170 kDa, FRAP1, NRG1, ESR1, ESR2, PGR, CDKN1B, MAP2K1, NEDD4-1, FOXO3A, PPP1R1B, PXN, ELA2, CTNNB1, AR, EPHB2, KLF6, ANXA7, NKX3-1, PITX2, MKI67, PHLPP, adiponectin (ADIPOQ), fibrinogen alpha chain (FGA), leptin (LEP), advanced glycosylation end product-specific receptor (AGER or RAGE), alpha-2-HS-glycoprotein (AHSG), angiogenin (ANG), CD14 molecule (CD14), ferritin (FTH1), insulin-like growth factor binding protein 1 (IGFBP1), interleukin 2 receptor, alpha (IL2RA), vascular cell adhesion molecule 1 (VCAM1) and Von Willebrand factor (VWF), myeloperoxidase (MPO), IL1α, TNFα, perinuclear anti-neutrophil cytoplasmic antibody (p-ANCA), lactoferrin, calprotectin, Wilm's tumor-1 protein, aquaporin-1, MLL3, AMBP, VDAC1, *E. coli* enterotoxins (heat-labile exotoxin, heat-stable enterotoxin), influenza HA antigen, tetanus toxin, diphtheria toxin, botulinum toxins, Shiga toxin, Shiga-like toxin I, Shiga-like toxin II, *Clostridium difficile* toxins A and B, etc.

Other examples of analytes include drugs of abuse (e.g. cocaine), protein biomarkers (including, but not limited to, nucleolin, nuclear factor-kB essential modulator (NEMO), CD-30, protein tyrosine kinase 7 (PTK7), vascular endothelial growth factor (VEGF), MUC1 glycoform, immunoglobulin p Heavy Chains (IGHM), Immunoglobulin E, αvβ3 integrin, α-thrombin, HIV gp120, NF-κB, E2F transcription factor, HER3, Plasminogen activator inhibitor, Tenascin C, CXCL12/SDF-1, prostate specific membrane antigen (PSMA), gastric cancer cells, and HGC-27); cells (including, but not limited to, non-small cell lung cancer (NSCLC), colorectal cancer cells, (DLD-1), H23 lung adenocarcinoma cells, Ramos cells, T-cell acute lymphoblastic leukemia (T-ALL) cells, CCRF-CEM, acute myeloid leukemia (AML) cells (HL60), small-cell lung cancer (SCLC) cells, NCIH69, human glioblastoma cells, U118-MG, PC-3 cells, HER-2-overexpressing human breast cancer cells, SK-BR-3, pancreatic cancer cells (Mia-PaCa-2)); and infectious agents (including, but not limited to, *Mycobacterium tuberculosis, Staphylococcus aureus, Shigella dysenteriae. Escherichia coli* O157:H7, *Campylobacter jejuni, Listeria monocytogenes, Pseudomonas aeruginosa, Salmonella* O8, *Salmonella enteritidis*).

Samples

The terms "sample," "test sample," and "biological sample" are used interchangeably herein and refer to a fluid sample containing or suspected of containing an analyte of interest. In some cases, the sample may comprise a liquid, fluent particulate solid, or fluid suspension of solid particles. In certain embodiments, the sample may be a liquid sample or a liquid extract of a solid sample. In some cases, the sample may be processed prior to the analysis described herein. For example, the sample may be separated or purified from its source prior to analysis; however, in certain embodiments, an unprocessed sample containing the analyte may be assayed directly. The sample may be derived from any suitable source. For example, the sample source may be synthetic (e.g., produced in a laboratory), the environment (e.g., air, soil, fluid samples, e.g., water supplies, etc.), an animal, e.g., a mammal, a plant, or any combination thereof. In a particular example, the sample is a human bodily substance (e.g., bodily fluid, blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited, to skeletal muscle tissue, liver tissue, lung tissue, kidney tissue, myocardial tissue, brain tissue, bone marrow, cervix tissue, skin, etc. In certain cases, the source of the sample may be an organ or tissue, such as a biopsy sample, which may be solubilized by tissue disintegration/cell lysis.

In some cases, the fluid sample may be diluted prior to use in an assay. For example, in embodiments where the source of an analyte molecule is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use.

In some cases, as mentioned above, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the sample is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

Specific Binding Members

The analyte of interest is captured on the surface of the solid support by way of a specific binding member attached to the solid support which specifically binds to the analyte. The terms "specific binding partner," "specific binding member," and "binding member" are used interchangeably herein and refer to one of two or more different molecules that specifically recognize the other molecule compared to substantially less recognition of other molecules. As will be appreciated by those in the art, an appropriate specific binding member will be determined by the analyte to be analyzed. In one embodiment, the solid support desirably comprises a plurality (e.g., 2 or more, 50 or more, 100 or more, 1,000 or more, or 5,000 or more) of specific binding members immobilized on the surface thereof which bind to an analyte of interest. Following a sufficient incubation time between the solid support and the sample, one or more analytes of interest present in the sample desirably are captured on the surface of the solid support via the specific binding members immobilized on the surface of the solid support. The term "immobilized," as used herein, refers to a stable association of a binding member with a surface of a solid support.

Binding members for a wide variety of target molecules are known or can be readily found or developed using known techniques. For example, when the target analyte is a protein, the binding members may include proteins, particularly antibodies or fragments thereof (e.g., antigen-binding fragments (Fabs), Fab' fragments, $F(ab')_2$ fragments, recombinant antibodies, chimeric antibodies, single-chain Fvs ("scFv"), single chain antibodies, single domain antibodies, such as variable heavy chain domains ("VHH"; also known as "VHH fragments") derived from animals in the Camelidae family (VHH and methods of making them are described in Gottlin et al., *Journal of Biomolecular Screening,* 14:77-85 (2009)), recombinant VHH single-domain antibodies, and $V_{NAR}$ fragments, disulfide-linked Fvs ("sdFv"), and anti-idiotypic ("anti-Id") antibodies, and functionally active epitope-binding fragments of any of the above, full-length polyclonal or monoclonal antibodies, antibody-like fragments, etc.), other proteins, such as receptor proteins, Protein A, Protein C, or the like. In embodiments where the analyte is a small molecule, such as a steroid, bilin, retinoid, or lipid, the first and/or the second binding member may be a scaffold protein (e.g., a lipocalin) or a receptor. In some cases, a binding member for protein analytes may be a peptide. For example, when the target analyte is an enzyme, suitable binding members may include enzyme substrates and/or enzyme inhibitors which may be a peptide, a small molecule, and the like. In some cases, when the target analyte is a phosphorylated species, a binding member may comprise a phosphate-binding agent. For example, the phosphate-binding agent may comprise metal-ion affinity media (see, e.g., U.S. Pat. No. 7,070,921 and U.S. Patent Application No. 2006/0121544).

In certain cases, a specific binding member may bean aptamer, such as those described in U.S. Pat. Nos. 5,270,163, 5,475,096, 5,567,588, 5,595,877, 5,637,459, 5,683,867, and 5,705,337. The term “aptamer” as used herein refers to a nucleic acid or peptide molecule that can bind to pre-selected targets including small molecules, proteins, and peptides among others with high affinity and specificity. Nucleic acid aptamers (e.g., single-stranded DNA molecules or single-stranded RNA molecules) may be developed for capturing virtually any target molecule. Aptamers bind target molecules in a highly specific, conformation-dependent manner, typically with very high affinity, although aptamers with lower binding affinity can be selected. Aptamers may distinguish between target analyte molecules based on very small structural differences such as the presence or absence of a methyl or hydroxyl group and certain aptamers can distinguish between D- and L-enantiomers and diastereomers. Aptamers may bind small molecular targets, including drugs, metal ions, and organic dyes, peptides, biotin, and proteins. Aptamers can retain functional activity after biotinylation, fluorescein labeling, and when attached to glass surfaces and microspheres.

Nucleic acid aptamers are oligonucleotides that may be single stranded oligodeoxynucleotides, oligoribonucleotides, or modified oligodeoxynucleotides or oligoribonucleotides. A “modified” oligodeoxynucleotide or oligoribonucleotide refers to nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl; 2-O-alkyl; 2-O-allyl; 2'-S-alkyl; 2'-S-allyl; 2'-fluoro-; 2'-halo or 2-azido-ribose, carbocyclic sugar analogues, anomeric sugars; epimeric sugars such as arabinose, xyloses or lyxoses, pyranose sugars, furanose sugars, and sedoheptulose.

Peptide aptamers may be designed to interfere with protein interactions. Peptide aptamers may be based on a protein scaffold onto which a variable peptide loop is attached, thereby constraining the conformation of the aptamer. In some cases, the scaffold portion of the peptide aptamer is derived from bacterial thioredoxin A (TrxA).

When the analyte is a carbohydrate, suitable binding members include, for example, antibodies, lectins, and selectins. As will be appreciated by those of ordinary skill in the art, any molecule that can specifically associate with an analyte of interest may potentially be used as a binding member.

In certain embodiments, suitable analyte/binding member complexes can include, but are not limited to, antibodies/antigens, antigens/antibodies, receptors/ligands, ligands/receptors, proteins/nucleic acid, enzymes/substrates and/or inhibitors, carbohydrates (including glycoproteins and glycolipids)/lectins and/or selectins, proteins/proteins, proteins/small molecules, etc.

In a particular embodiment, a specific binding member may be attached to a solid support via a linkage, which may comprise any moiety, functionalization, or modification of the support and/or binding member that facilitates the attachment of the binding member to the support. The linkage between the binding member and the support may include one or more chemical or physical (e.g., non-specific attachment via van der Waals forces, hydrogen bonding, electrostatic interactions, hydrophobic/hydrophilic interactions; etc.) bonds and/or chemical spacers providing such bond(s). Certain embodiments utilize binding members that are proteins or polypeptides. As is known in the art, any number of techniques may be used to attach a polypeptide to a wide variety of solid supports (see, e.g., U.S. Pat. No. 5,620,850; and Heller, *Acc. Chem. Res.,* 23: 128 (1990)).

In certain embodiments, a solid support may also comprise a protective, blocking, or passivating layer that can eliminate or minimize non-specific attachment of non-capture components (e.g., analyte molecules, binding members) to the binding surface during the assay which may lead to false positive signals during detection or to loss of signal. Examples of materials that may be utilized in certain embodiments to form passivating layers include, but are not limited to polymers (e.g., polyethylene glycol) that repel the non-specific binding of proteins; naturally occurring proteins (e.g., serum albumin and casein); surfactants (e.g., zwitterionic surfactants, sulfobetaines); naturally occurring long-chain lipids; polymer brushes, and nucleic acids, such as salmon sperm DNA.

As explained herein, binding between the binding members and the analyte is specific, e.g., as when the binding member and the analyte are complementary parts of a binding pair. In certain embodiments, the binding member binds specifically to the analyte. By “specifically bind” or “binding specificity,” it is meant that the binding member binds the analyte molecule with specificity sufficient to differentiate between the analyte molecule and other components or contaminants of the sample. For example, the binding member, according to one embodiment, may be an antibody that binds specifically to an epitope on an analyte. The antibody, according to one embodiment, can be any antibody capable of binding specifically to an analyte of interest. For example, appropriate antibodies include, but are not limited to, monoclonal antibodies, bispecific antibodies, minibodies, domain antibodies (dAbs) (e.g., such as described in Holt et al., *Trends in Biotechnology,* 21: 484-490 (2014), and including single domain antibodies sdAbs that are naturally occurring, as in cartilaginous fishes and camelid, or which are synthetic, e.g., nanobodies, VHH, or other domain structure), synthetic antibodies (sometimes referred to as antibody mimetics), chimeric antibodies, humanized antibodies, antibody fusions (sometimes referred to as “antibody conjugates”), and antibody fragments as described above. As another example, the analyte molecule may be an antibody and the corresponding binding member may be an antigen.

In embodiments where the analyte is a biological cell (e.g., mammalian, avian, reptilian, other vertebrate, insect, yeast, bacterial, cell, etc.), binding members may be ligands having specific affinity for a cell surface antigen (e.g., a cell surface receptor). In one embodiment, the binding member may be an adhesion molecule receptor or portion thereof, which has binding specificity for a cell adhesion molecule expressed on the surface of a target cell type. In use, the adhesion molecule receptor binds with an adhesion molecule on the extracellular surface of the target cell, thereby immobilizing or capturing the cell, the bound cell may then be detected by using a second binding member that may be the same as the first binding member or may bind to a different molecule expressed on the surface of the cell.

In some embodiments, the binding affinity between analyte molecules and binding members should be sufficient to remain bound under the conditions of the assay, including wash steps to remove molecules or particles that are non-specifically bound. In some cases, for example in the detection of certain biomolecules, the binding constant of the analyte molecule to its complementary binding member may be between at least about $10^4$ and about $10^6$ $M^{-1}$, at least about $10^5$ and about $10^9$ $M^{-1}$, at least about $10^7$ and about $10^9$ $M^{-1}$, greater than about $10^9$ $M^{-1}$, or greater.

Loading Array of Wells

The disclosed method comprises contacting an array of wells with a liquid droplet. The array of wells includes a plurality of individual wells. The array of wells may include a plurality of wells that may range from 10 to $10^9$ n number per 1 $mm^2$. In certain cases, an array of about 100,000 to 500,000 wells (e.g., femtoliter wells) covering an area approximately 12 $mm^2$ may be fabricated. Each well may measure about 4.2 μm wide×3.2 μm deep (volume approximately 50 femtoliters), and ideally is capable of holding a single bead/particle (about 3 μm diameter) or is of sufficient size to have loaded therein a portion of a single liquid droplet. At this density, the femtoliter wells are spaced at a distance of approximately 7.4 μm from each other. In some examples, the well array may be fabricated to have individual wells with a diameter of 10 nm to 10,000 nm.

The wells may be any of a variety of shapes, such as, for example, cylindrical with a flat bottom surface, cylindrical with a rounded bottom surface, cubical, cuboidal, frustoconical, inverted frustoconical, or conical. In certain cases, the wells may include a sidewall that may be oriented to facilitate the receiving and retaining of a microbead or microparticle present in liquid droplets that have been moved over the well array. In some embodiments, the wells may include a first sidewall and a second sidewall, where the first sidewall may be opposite the second side wall. In some examples, the first sidewall is oriented at an obtuse angle with reference to the bottom of the wells and the second sidewall is oriented at an acute angle with reference to the bottom of the wells. The movement of the droplets may be in a direction parallel to the bottom of the wells and from the first sidewall to the second sidewall.

In some examples, the array of wells can be fabricated through molding, pressure, heat, or laser, or a combination thereof. In some examples, the array of wells may be fabricated using nanoimprint/nanosphere lithography. Other fabrication methods well known in the art may also be used In certain embodiments, the array of wells used in the method have a hydrophobic surface. In other embodiments, the array of wells has a hydrophilic surface.

The methods described herein further comprise moving the liquid droplet over the array of wells (where one or more wells of the array are of sufficient size to accommodate the at least one solid support). In some embodiments, movement of the liquid droplet over the well array is achieved by using energy to exert a force to manipulate the liquid droplets. The phrase "using energy to exert a force to manipulate the liquid droplet," as used herein, refers to the use of non-mechanical forces (namely, for example, energy created without the use of pumps and/or valves) to provide or exert a force that manipulates (e.g., moves or merges) at least a portion of the liquid droplet across or over the array of wells. Examples of non-mechanical forces that can be used in the methods described herein include electric actuation force (such as droplet actuation, electrophoresis, electrowetting, dielectrophoresis, electrostatic actuation, electric field mediated, electrode mediated, capillary force, chromatography, centrifugation, or aspiration) and/or acoustic force (such as surface acoustic wave (or "SAW")). In certain embodiments, an electric actuation force is employed. For example, the electric actuation force may be an alternating current. In some embodiments, the alternating current can have a root mean squared (rms) voltage of 10V, 15V, 20V, 25V, 30V, 35V or more. For example, such alternating current can have a rms voltage of 10V or more, 15V or more, 20V or more, 25V or more, 30V or more, or 35V or more. Alternatively, the alternating current can have a frequency in a radio frequency range.

In certain embodiments, if magnetic solid supports are used, an electric actuation force and a magnetic field can be applied from opposition directions, relative to the at least a portion of the one or more liquid droplets. In certain embodiments, an electric actuation force can be generated using a series or plurality of electrodes (namely, at least two or more, at least three or more, at least four or more, at least five or more, at least six or more, at least seven or more, at least eight or more, at least nine or more, at least ten or more, at least eleven or more, at least twelve or more, at least thirteen or more, at least fourteen or more, at least fifteen or more, etc.) to move the liquid droplet to and over the array of wells. In some embodiments, the method further includes positioning the liquid droplet over the array of wells using a capillary element configured to facilitate movement of the liquid droplet to the array of wells.

In certain embodiments, the moving of the liquid droplet to and over an array of wells results in the loading (filling and/or placement) of one or more portions of the liquid droplet, and a solid support contained therein, into the wells of the array. In certain embodiments, a magnetic field is used to facilitate movement of the liquid droplet and thus, at least one solid support, into one or more wells of the array. As discussed above, the presence of the surfactant or detergent in the liquid droplet is believed to relieve the trapped air in the "Cassie State," which describes the effective contact angle θc for a liquid on a composite surface (Cassie, A. B. D. and Baxter, S., *Transactions of the Faraday Society,* 40: 546 (1944)). The surfactant or detergent reduces the contact angle of the droplet and a microwell or nanowell, resulting in more efficient droplet loading and wetting of wells. In certain embodiments, after the liquid droplet is loaded into the wells, any portions of the liquid droplet that are not loaded into a well can be removed using routine techniques known in the art. For example, such removing can involve generating an electric actuation force (such as described previously herein) with a series or plurality of electrodes to move a fluid droplet (such as a polarizable fluid droplet) to the array of wells to move at least a portion of the mixture to a distance (the length of which is not critical) from the array of wells. In certain embodiments, an aqueous washing liquid can be used to remove portions of a liquid droplet not loaded into a well. In such embodiments, the removal involves generating an electric actuation force with a series or plurality of electrodes to move an aqueous wash (or washing) droplet across the array of wells. The amount and type of aqueous liquid used for said washing is not critical. Following wash steps to remove any portion of a liquid droplet not located inside the wells, the method comprises sealing the loaded wells. The loaded wells may be sealed using any suitable method or composition. In one embodiment, the wells may be sealed by moving a hydrophobic liquid (e.g., an oil) over the loaded wells using an external force as described herein.

Analyte Detection and Quantification

Also provided herein is a method of detecting and quantifying an analyte of interest in a sample, which method comprises (a) providing a first liquid droplet containing an analyte of interest; (b) providing a second liquid droplet containing a solid support which comprises a binding member that specifically binds to the analyte of interest; wherein either the first liquid droplet or the second liquid droplet further comprises a detergent or surfactant; (c) using energy to exert a force to manipulate the first liquid droplet and the second liquid droplet to create a droplet mixture comprising one or more liquid droplets each of which comprises an analyte of interest captured on the surface of the solid support; (d) loading wells in an array with the one or more liquid droplets according to the methods described herein; and (e) detecting and quantifying the analyte of interest. Descriptions of the analyte of interest, sample, liquid droplet and portions thereof, solid support, detergent or surfactant, and loading of wells set forth above in connection with other embodiments of the disclosure also are applicable to those same aspects of the aforesaid method of detecting and quantifying an analyte of interest. Similar to the movement of the liquid droplet over a well array described above, the analyte detection method involves the use of energy to exert a force to manipulate the first liquid droplet and the second liquid droplet to create a droplet mixture. For example, non-mechanical forces may be used to provide or exert a force that manipulates (such as merges or combines) at least the first and second liquid droplets (and optionally, additional droplets) into a mixture. Example of non-mechanical forces that can be used in the methods described herein include electric actuation force (such as droplet actuation, electrophoresis, electrowetting, dielectrophoresis, electrostatic actuation, electric field mediated, electrode mediated, capillary force, chromatography, centrifugation or aspiration) and/or acoustic force (e.g., SAW). In certain embodiments, the electric actuation force generated is an alternating current, such as is described above.

As described elsewhere herein, one or more of the first droplet, the second droplet, and the droplet mixture may comprise an aqueous liquid or immiscible liquid. In other embodiments, one or more of the first droplet, the second droplet, and the droplet mixture may be hydrophobic liquid droplets. In other embodiments, one or more of the first droplet, the second droplet, and the droplet mixture may be hydrophilic liquid droplets. In certain embodiments, one or more of the first droplet, the second droplet, and the droplet mixture is a polarizable liquid.

The methods described herein involve detecting and quantifying the analyte of interest in the sample. To this end, in some embodiments, a detectable label is added to the droplet mixture before loading wells in an array with the one or more liquid droplets. Alternatively, a detectable label may be added to the droplet mixture after loading wells in an array with the droplet mixture. In other embodiments, the first or second droplet may comprise a detectable label prior to their manipulation to create a droplet mixture.

The terms "label" and "detectable label" may be used interchangeably herein to refer to a moiety attached to a specific binding member or analyte to render the reaction between the specific binding member and the analyte detectable, and the specific binding member or analyte so labeled is referred to as "detectably labeled." A label can produce a signal that is detectable by visual or instrumental means. Various labels include: (i) a tag attached to a specific binding member or analyte by a cleavable linker, or (ii) signal-producing substance, such as chromagens, fluorescent compounds, enzymes, chemiluminescent compounds, radioactive compounds, and the like. Representative examples of labels include moieties that produce light, e.g., acridinium compounds, and moieties that produce fluorescence, e.g., fluorescein. Other labels are known in the art (see, e.g., WO 2016/161400A1) and may be used in the disclosed methods. In other embodiments, a moiety itself may not be detectable but may become detectable upon reaction with yet another moiety. Use of the term "detectably labeled" is intended to encompass such labeling.

In certain embodiments, the detectable label comprises at least one binding member that specifically binds to the analyte of interest. The detectable label may comprise a chromagen, a florescent compound, an enzyme, a chemiluminescent compound, or a radioactive compound. In certain embodiments, the binding member is a receptor, aptamer, or antibody.

Any suitable signal-producing substance known in the art can be used as a detectable label. For example, the detectable label can be a radioactive label (such as $^{3}H$, $^{14}C$, $^{32}P$ $^{33}P$, $^{35}S$, $^{90}Y$, $^{99}Tc$, $^{111}In$, $^{125}I$, $^{131}I$, $^{177}Lu$, $^{166}Ho$, and $^{153}Sm$), an enzymatic label (such as horseradish peroxidase, alkaline peroxidase, glucose 6-phosphate dehydrogenase, and the like (if enzymes are used then a corresponding enzymatic substrate must also be added)), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachloro-fluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. Labels, labeling procedures, and detection of labels is described in, e.g., Polak and Van Noorden, *Introduction to Immunocytochemistry,* 2nd ed., Springer Verlag, N.Y. (1997), and in Haugland, *Handbook of Fluorescent Probes and Research Chemicals*, Molecular Probes, Inc., Eugene, Oregon (1996). The use of fluorescent labels in analyte detection assays also is described in, for example, Adamczyk et al., *Bioorg. Med. Chem. Lett.,* 16:1324-1328 (2006); Adamczyk et al., *Bioorg. Med. Chem. Lett.,* 4: 2313-2317 (2004); Adamczyk et al., *Biorg. Med. Chem. Lett.,* 14: 3917-3921 (2004); and Adamczyk et al., *Org. Lett.,* 5: 3779-3782 (2003).

It will be appreciated that the sample and the first binding member may be incubated for a sufficient period of time to allow for the binding interaction between the binding member and analyte to occur. In addition, the incubating may be in a binding buffer that facilitates the specific binding interaction. The binding affinity and/or specificity of a binding member may be manipulated or altered in the assay by varying the binding buffer. In some embodiments, the binding affinity and/or specificity may be increased by varying the binding buffer. In some embodiments, the binding affinity and/or specificity may be decreased by varying the binding buffer.

The binding buffer may include molecules typically used in antigen-antibody binding buffers such as, albumin (e.g., BSA), non-ionic detergents (Tween-20, Triton X-100), and/or protease inhibitors (e.g., PMSF). In certain cases, the binding buffer may be added to a microfluidic chip, chamber, etc., prior to or after adding the sample. In other embodiments, a binding member may be present in a binding buffer prior to contacting with the sample. The length of time for binding interaction between the binding member and analyte to occur may be determined empirically and may depend on the binding affinity and binding avidity between the binding member and the analyte. In certain embodiments, the contacting or incubating may be for a period of 5 seconds to 1 hour, such as, 10 seconds-30 minutes, or 1 minute-15 minutes, or 5 minutes-10 minutes, e.g., 10 seconds, 15 seconds, 30 seconds, 1 minute, 5 minutes, 10 minutes, 15 minutes, 30 minutes, 45 minutes, 1 hour or 2 hours. Other conditions for the binding interaction, such as, temperature and salt concentration, may also be determined empirically or may be based on manufacturer's instructions. For example, the contacting may be carried out at room temperature (21° C.-28° C., e.g., 23° C.-25° C.), 37° C., or 4° C. In certain embodiments, an optional mixing of the sample with the first binding member may be carried out during the contacting step.

Following analyte capture on the solid support via the first binding member (i.e., formation of a "complex" comprising the first binding member and analyte), any unbound analyte may be removed from the vicinity of the first binding member along with the sample, while the complex of the first binding member and the analyte may be retained due to its association with the solid support. Optionally, the solid support may be contacted with a wash buffer to remove any molecules non-specifically bound to the solid support.

Following complex formation between an immobilized first binding member and an analyte, and the optional removal of sample and/or wash steps, the complex of the first binding member and the analyte may be contacted with a second binding member that specifically binds to the analyte of interest, thereby leading to the formation of a sandwich complex in which the analyte is bound by the two binding members. An optional mixing of the second member with the first binding member-analyte complex may be carried out. In some embodiments, immobilization of the analyte molecules with respect to a surface may aid in removal of any excess second binding members from the solution without concern of dislodging the analyte molecule from the surface. In some embodiments, as discussed herein, the second binding member may include a detectable label comprising one or more signal-producing substances, such as chromagens, fluorescent compounds, chemiluminescent compounds, enzymes, radioactive compounds, and the like.

Following contact with a second binding member, any unbound second binding member may be removed, followed by an optional wash step. Any unbound second binding member may be separated from the complex of the first binding member-analyte-second binding member by a suitable means such as, droplet actuation, electrophoresis, electrowetting, dielectrophoresis, electrostatic actuation, electric field mediated, electrode mediated, capillary force, chromatography, centrifugation, aspiration, or SAW. Upon removal of any unbound second binding member from the vicinity of the complex of the first binding member-analyte-second binding member, the detectable label attached to the second binding member present in the complex of the first binding member-analyte-second binding member may be separated by a suitable means or may be detected using techniques known in the art.

In certain embodiments, the method described herein is performed using a microfluidics device, such as a digital microfluidics device. The terms "digital microfluidics (DMF)," "digital microfluidic module (DMF module)," or "digital microfluidic device (DMF device)" are used interchangeably herein to refer to a module or device that utilizes digital or droplet-based microfluidic techniques to provide for manipulation of discrete and small volumes of liquids in the form of droplets. Digital microfluidics uses the principles of emulsion science to create fluid-fluid dispersion into channels (principally water-in-oil emulsion). It allows the production of monodisperse drops/bubbles or with a very low polydispersity. Digital microfluidics is based upon the micromanipulation of discontinuous fluid droplets within a reconfigurable network. Complex instructions can be programmed by combining the basic operations of droplet formation, translocation, splitting, and merging.

Digital microfluidics operates on discrete volumes of fluids that can be manipulated by binary electrical signals. By using discrete unit-volume droplets, a microfluidic operation may be defined as a set of repeated basic operations, i.e., moving one unit of fluid over one unit of distance. Droplets may be formed using surface tension properties of the liquid. Actuation of a droplet is based on the presence of electrostatic forces generated by electrodes placed beneath the bottom surface on which the droplet is located. Different types of electrostatic forces can be used to control the shape and motion of the droplets. One technique that can be used to create the foregoing electrostatic forces is based on dielectrophoresis which relies on the difference of electrical permittivities between the droplet and surrounding medium and may utilize high-frequency AC electric fields. Another technique that can be used to create the foregoing electrostatic forces is based on electrowetting which relies on the dependence of surface tension between a liquid droplet present on a surface and the surface on the electric field applied to the surface.

In certain embodiments, the method described herein is performed using a surface acoustic wave-based microfluidics device (SAW). In certain embodiments, the method described herein is performed using an integrated DMF and analyte detection device. In certain embodiments, the method described herein is performed using an integrated SAW-based microfluidic device and analyte detection device. In certain embodiments, the method described herein is performed using a Robotics based assay processing unit.

The method may involve single molecule counting. In certain embodiments, the method involves determining the presence of and/or concentration of an analyte in a sample. In certain embodiments, the method may also be used for determining presence of and/or concentration of a plurality of different analytes present in a sample (i.e., multiplexing).

In certain embodiments, quantifying the analyte of interest first involves determining the total number of solid supports in the well of the array ("total solid support number"). Next, the number of solid supports in the wells of the array that contain the detectable label are determined, such as, for example, determining the intensity of the signal produced by the detectable label ("positives"). The positives are subtracted from the total solid support number to provide the number of solid supports in the array of wells that do not contain a detectable label or are not detected ("negatives"). Then, the ratio of positives to negatives in the array of wells can be determined and compared to a calibration curve. Analyte concentration can be quantified using analog or digital read-out. For example, for high numbers of positive wells (>70%) the relative intensities of signal-bearing wells may be compared to the signal intensity generated from a single bead/particle/analyte molecule, respectively, and used to generate an analog signal. Alternatively, for a low number of positive wells (<70% positive) digital quantitation using the Poisson equation $P(x; \mu)$ may be employed, as shown below:

$$P(x;\mu)=(e^{-\mu})(\mu^{x})/x!$$

where:

e: is a constant equal to approximately 2.71828,

μ: is the mean number of successes that occur in a specified region, and x: is the tactual number of successes that occur in a specified region.

Thus, a digital signal may be used for lower analyte concentrations, whereas an analog signal may be used for higher analyte concentrations. A combination of digital and analog quantitation may be used, which may expand the linear dynamic range.

In certain embodiments, the simultaneous analysis of multiple analytes in a single sample may be performed by using a plurality of different first and second binding members where a pair of first and second binding members is specific to a single analyte in the sample. In these embodiments, the detectable label associated with the second binding member of a first pair of first and second binding members specific to a single analyte may be distinguishable from the detectable label associated with the second binding member of a second pair of first and second binding members specific to a different analyte. A first detectable label may be distinguishable from second detectable label based on difference in signal-producing substances, and the like In some embodiments, the concentration of an analyte in a sample that may be substantially accurately determined is less than about 5000 fM (femtomolar), less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less. For example, the concentration of analyte in the sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM, or a range defined by any of two of the foregoing values.

In some embodiments, the lower limit of detection (e.g., the lowest concentration of an analyte which may be determined in solution) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less.

The upper limit of detection (e.g., the upper concentration of an analyte which may be determined in solution) may be at least about 100 fM, at least about 1000 fM, at least about 10 pM (picomolar), at least about 100 pM, at least about 100 pM, at least about 10 nM (nanomolar), at least about 100 nM, at least about 1000 nM, at least about 10 pM, at least about 100 pM, at least about 1000 μM, at least about 10 mM, at least about 100 mM, at least about 1000 mM, or greater.

In some cases, the presence and/or concentration of the analyte in a sample may be detected rapidly, usually in less than about 1 hour, e.g., 45 minutes, 30 minutes, 15 minutes, 10 minutes, 5 minutes, 1 minute, or 30 seconds.

The disclosed method may comprise quality control components. "Quality control components" in the context of immunoassays and kits described herein include, but are not limited to, calibrators, controls, and sensitivity panels. A "calibrator" or "standard" can be used (e.g., one or more, such as a plurality) in order to establish calibration (standard) curves for interpolation of the concentration of an analyte, such as an antibody. Alternatively, a single calibrator, which is near a reference level or control level (e.g., "low", "medium", or "high" levels), can be used. Multiple calibrators (i.e., more than one calibrator or a varying amount of calibrator(s)) can be used in conjunction to comprise a "sensitivity panel." The calibrator is optionally part of a series of calibrators in which each of the calibrators differs from the other calibrators in the series, such as, for example, by concentration or detection method (e.g., colorimetric or fluorescent detection).

Variations on the Disclosed Methods

The disclosed methods may be adapted as appropriate in view of other methods for analyzing analytes. Examples of well-known variations include, but are not limited to, immunoassay, such as sandwich immunoassay (e.g., monoclonal-polyclonal sandwich immunoassays), immunoassay including enzyme detection (enzyme immunoassay (EIA) or enzyme-linked immunosorbent assay (ELISA)), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc. In some instances, the descriptions below may overlap the method described above; in others, the descriptions below may provide alternates.

Immunoassay

The analyte of interest, and/or peptides or fragments thereof, may be analyzed using an immunoassay. Any immunoassay may be utilized. The immunoassay may be an enzyme-linked immunoassay (ELISA), a competitive inhibition assay, such as forward or reverse competitive inhibition assays, or a competitive binding assay, for example. In some embodiments, a detectable label (e.g., such as one or more fluorescent labels) is attached to a capture antibody and/or a detection antibody.

A heterogeneous format may be used. For example, after a sample is obtained from a subject, a first mixture is prepared. The mixture contains the sample being assessed for analyte of interest and a first specific binding member, wherein the first specific binding member and any analyte of interest contained in the sample to form a first specific binding member-analyte of interest complex. Preferably, the first specific binding member is an anti-analyte of interest antibody or a fragment thereof. The order in which the sample and the first specific binding member are added to form the mixture is not critical. Preferably, the first specific binding member is immobilized on a solid phase. The solid phase used in the immunoassay (for the first specific binding member and, optionally, the second specific binding member) can be any solid phase known in the art, such as, but not limited to, a magnetic particle, a bead, a nanobead, a microbead, a nanoparticle, a microparticle, a membrane, a scaffolding molecule, a film, a filter paper, a disc, or a chip (e.g., a microfluidic chip).

After the mixture containing the first specific binding member-analyte of interest complex is formed, any unbound analyte of interest is removed from the complex using any technique known in the art. For example, the unbound analyte of interest can be removed by washing. Desirably, however, the first specific binding member is present in excess of any analyte of interest present in the sample, such that all analyte of interest that is present in the sample is bound by the first specific binding member.

After any unbound analyte of interest is removed, a second specific binding member is added to the mixture to form a first specific binding member-analyte of interest-second specific binding member complex. The second specific binding member is preferably an anti-analyte of interest (such as an antibody) that binds to an epitope on analyte of interest that differs from the epitope on analyte of interest bound by the first specific binding member. Moreover, also preferably, the second specific binding member is labeled with or contains a detectable label (e.g., a detectable label, a tag attached by a cleavable linker, etc.).

The use of immobilized antibodies or fragments thereof may be incorporated into the immunoassay. The antibodies may be immobilized onto a variety of supports, such as magnetic or chromatographic matrix particles, latex particles or modified surface latex particles, polymer or polymer film, plastic or plastic film, planar substrate, a microfluidic surface, pieces of a solid substrate material, and the like.

Sandwich Immunoassay

A sandwich immunoassay measures the amount of antigen between two layers of antibodies (i.e., a capture antibody (i.e., at least one capture antibody) and a detection antibody (i.e. at least one detection antibody)). The capture antibody and the detection antibody bind to different epitopes on the antigen, e.g., analyte of interest. Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte of interest in a sample. More specifically, the at least two antibodies bind to certain epitopes of analyte of interest or an analyte of interest fragment forming an immune complex which is referred to as a "sandwich." One or more antibodies can be used to capture the analyte of interest in the sample (these antibodies are frequently referred to as a "capture" antibody or antibodies), and one or more antibodies with a detectable label (e.g., a fluorescent label, a tag attached by a cleavable linker, etc.) that also bind the analyte of interest (these antibodies are frequently referred to as the "detection" antibody or antibodies) can be used to complete the sandwich. In some embodiments, an aptamer may be used as the second binding member. In a sandwich assay, the binding of an antibody to its epitope desirably is not diminished by the binding of any other antibody in the assay to its respective epitope. In other words, antibodies are selected so that the one or more first antibodies brought into contact with a sample suspected of containing analyte of interest do not bind to all or part of an epitope recognized by the second or subsequent antibodies, thereby interfering with the ability of the one or more second detection antibodies to bind to the analyte of interest.

In one embodiment, a sample suspected of containing analyte of interest can be contacted with at least one capture antibody (or antibodies) and at least one detection antibodies either simultaneously or sequentially. In the sandwich assay format, a sample suspected of containing analyte of interest (such as a membrane-associated analyte of interest, a soluble analyte of interest, fragments of membrane-associated analyte of interest, fragments of soluble analyte of interest, variants of analyte of interest (membrane-associated or soluble analyte of interest) or any combinations thereof)) is first brought into contact with the at least one capture antibody that specifically binds to a particular epitope under conditions which allow the formation of an antibody-analyte of interest complex. If more than one capture antibody is used, a multiple capture antibody-analyte of interest complex is formed. In a sandwich assay, the antibodies, preferably, the at least one capture antibody, are used in molar excess amounts of the maximum amount of analyte of interest or the analyte of interest fragment expected in the sample.

Optionally, prior to contacting the sample with the at least one first capture antibody, the at least one capture antibody can be bound to a solid support which facilitates the separation the antibody-analyte of interest complex from the sample. Any solid support known in the art can be used, including but not limited to, solid supports made out of polymeric materials in the form of planar substrates or beads, and the like. The antibody (or antibodies) can be bound to the solid support by adsorption, by covalent bonding using a chemical coupling agent or by other means known in the art, provided that such binding does not interfere with the ability of the antibody to bind analyte of interest or analyte of interest fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide, azido, alkynyl, and 1-ethyl-3-(3-dimethylaminopropyl)carbodiimide.

After the sample suspected of containing analyte of interest is brought into contact with the at least one capture antibody, the sample is incubated in order to allow for the formation of a capture antibody (or capture antibodies)-analyte of interest complex. The incubation can be carried out at a pH of from about 4.5 to about 10.0, at a temperature of from about 2° C. to about 45° C., and for a period from at least about one minute to about eighteen (18) hours, from about 2-6 minutes, or from about 3-4 minutes.

After formation of the capture antibody (antibodies)-analyte of interest complex, the complex is then contacted with at least one detection antibody (under conditions which allow for the formation of a capture antibody (antibodies)-analyte of interest-detection antibody (antibodies) complex). If the capture antibody-analyte of interest complex is contacted with more than one detection antibody, then a capture antibody (antibodies)-analyte of interest-detection antibody (antibodies) detection complex is formed. As with the capture antibody, when the at least one detection (and subsequent) antibody is brought into contact with the capture antibody-analyte of interest complex, a period of incubation under conditions similar to those described above is required for the formation of the capture antibody (antibodies)-analyte of interest-detection antibody (antibodies) complex. Preferably, at least one detection antibody contains a detectable label (e.g., a fluorescent label, a tag attached by a cleavable linker, etc.). The detectable label can be bound to the at least one detection antibody prior to, simultaneously with or after the formation of the capture antibody (antibodies)-analyte of interest-detection antibody (antibodies) complex. Any detectable label known in the art can be used, e.g., a fluorescent label, a cleavable linker as discussed herein, and others known in the art.

The order in which the sample and the specific binding member(s) are added to form the mixture for assay is not critical. If the first specific binding member is detectably labeled (e.g., a fluorescent label, a tag attached with a cleavable linker, etc.), then detectably-labeled first specific binding member-analyte of interest complexes form. Alternatively, if a second specific binding member is used and the second specific binding member is detectably labeled (e.g., a fluorescent label, a tag attached with a cleavable linker, etc.), then detectably-labeled complexes of first specific binding member-analyte of interest-second specific binding member form. Any unbound specific binding member, whether labeled or unlabeled, can be removed from the mixture using any technique known in the art, such as washing.

Next, signal, indicative of the presence of analyte of interest or a fragment thereof is generated. Based on the parameters of the signal generated, the amount of analyte of interest in the sample can be quantified. Optionally, a standard curve can be generated using serial dilutions or solutions of known concentrations of analyte of interest by mass spectroscopy, gravimetric methods, and other techniques known in the art.

Forward Competitive Inhibition

In a forward competitive format, an aliquot of labeled analyte of interest (e.g., analyte having a fluorescent label, a tag attached with a cleavable linker, etc.) of a known concentration is used to compete with analyte of interest in a sample for binding to analyte of interest antibody.

In a forward competition assay, an immobilized specific binding member (such as an antibody) can either be sequentially or simultaneously contacted with the sample and a labeled analyte of interest, analyte of interest fragment or analyte of interest variant thereof. The analyte of interest peptide, analyte of interest fragment or analyte of interest variant can be labeled with any detectable label, including a detectable label comprised of tag attached with a cleavable linker. In this assay, the antibody can be immobilized on to a solid support. Alternatively, the antibody can be coupled to an antibody, such as an antispecies antibody, that has been immobilized on a solid support, such as a microparticle or planar substrate.

Reverse Competition Assay

In a reverse competition assay, an immobilized analyte of interest can either be sequentially or simultaneously contacted with a sample and at least one labeled antibody. The analyte of interest can be bound to a solid support, such as the solid supports discussed above in connection with the sandwich assay format.

One-Step Immunoassay or "Capture on the Fly"

In a capture on the fly immunoassay, a solid substrate is pre-coated with an immobilization agent. The capture agent, the analyte and the detection agent are added to the solid substrate together, followed by a wash step prior to detection. The capture agent can bind the analyte and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody.

In certain other embodiments, in a one-step immunoassay or "capture on the fly", a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is streptavidin, the ligand on the first specific binding member may be biotin) and also binds to the analyte of interest. The second specific binding member comprises a detectable label and binds to an analyte of interest. The solid support and the first and second specific binding members may be added to a sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the detectable label is detected. An optional wash step may be employed before the detection. In certain embodiments, in a one-step assay more than one analyte may be measured. In certain other embodiments, more than two specific binding members can be employed. In certain other embodiments, multiple detectable labels can be added. In certain other embodiments, multiple analytes of interest can be detected.

The use of a capture on the fly assay can be done in a variety of formats as described herein, and known in the art. For example, the format can be a sandwich assay such as described above, but alternately can be a competition assay, can employ a single specific binding member, or use other variations such as are known.

Combination Assays

In a combination assay, a solid substrate, such as a microparticle, is co-coated with an antigen and an antibody to capture an antibody and an antigen from a sample, respectively. The solid support may be co-coated with two or more different antigens to capture two or more different antibodies from a sample. The solid support may be co-coated with two or more different antibodies to capture two or more different antigens from a sample.

Additionally, the methods described herein may use blocking agents to prevent either specific or non-specific binding reactions (e.g., HAMA concern) among assay compounds. Once the agent (and optionally, any controls) is immobilized on the support, the remaining binding sites of the agent may be blocked on the support. Any suitable blocking reagent known to those of ordinary skill in the art may be used. For example, bovine serum albumin ("BSA"), phosphate buffered saline ("PBS") solutions of casein in PBS, Tween 20™ (Sigma Chemical Company, St. Louis, Mo.), or other suitable surfactant, as well as other blocking reagents, may be employed.

As is apparent from the present disclosure, the methods disclosed herein, including variations, may be used for diagnosing a disease, disorder or condition in a subject suspected of having the disease, disorder, or condition. For example, the sample analysis may be useful for detecting a disease marker, such as, a cancer marker, a marker for a cardiac condition, a toxin, a pathogen, such as, a virus, a bacterium, or a portion thereof. The methods also may be used for measuring analyte present in a biological sample. The methods also may be used in blood screening assays to detect a target analyte. The blood screening assays may be used to screen a blood supply.

The following example further illustrates the invention but, of course, should not be construed as in any way limiting its scope.

Example

This example describes the influence of detergents on seeding efficiency in plastic microarrays.

Figures 2A, 2B:
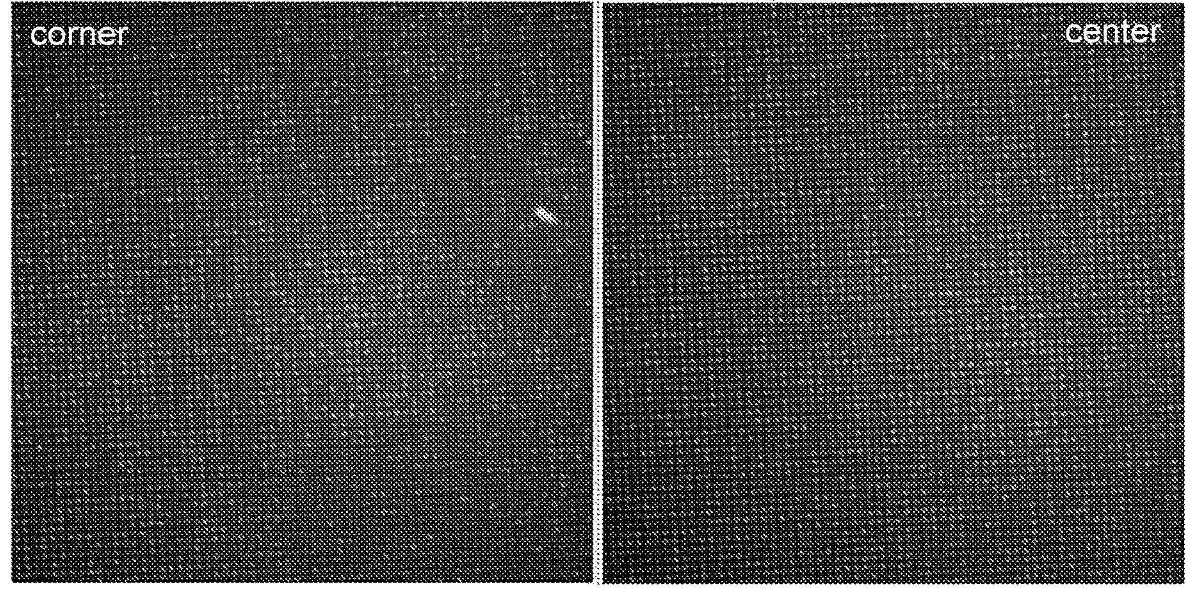
FIGS. 2A and 2B are images of the corner (FIG. 2A) and center (FIG. 2B) of a nanowell plate loaded with droplets comprising the detergent Tetronic 90R4.
Figures 3A, 3B:
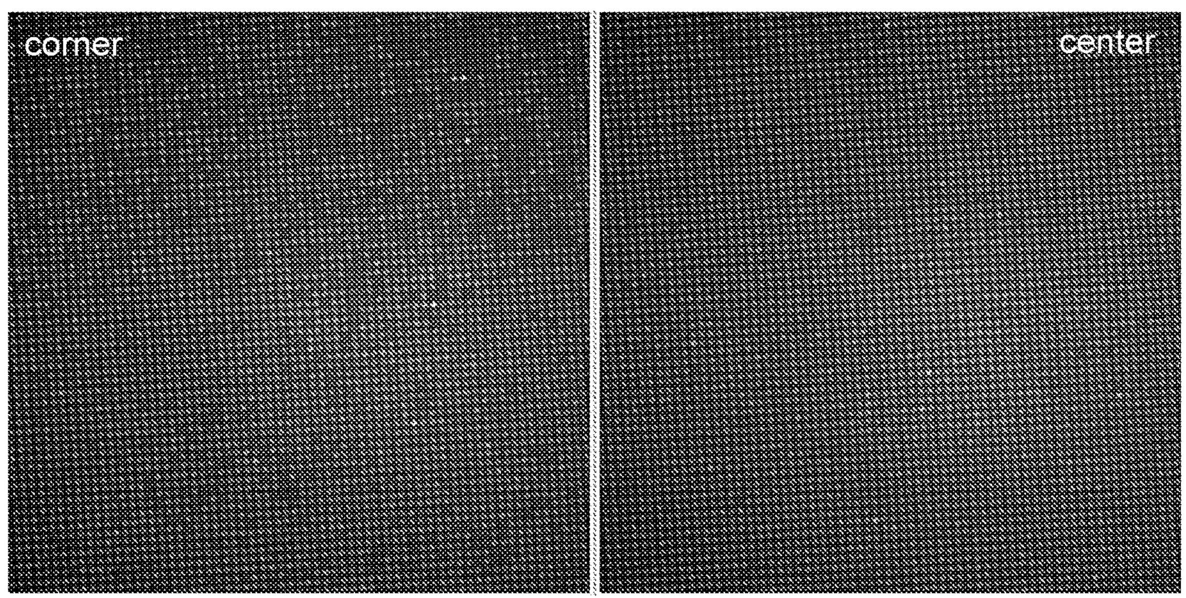
FIGS. 3A and 3B are images of the corner (FIG. 3A) and center (FIG. 3B) of a nanowell plate loaded with droplets comprising the detergent Tween 20.
Figures 4A, 4B:
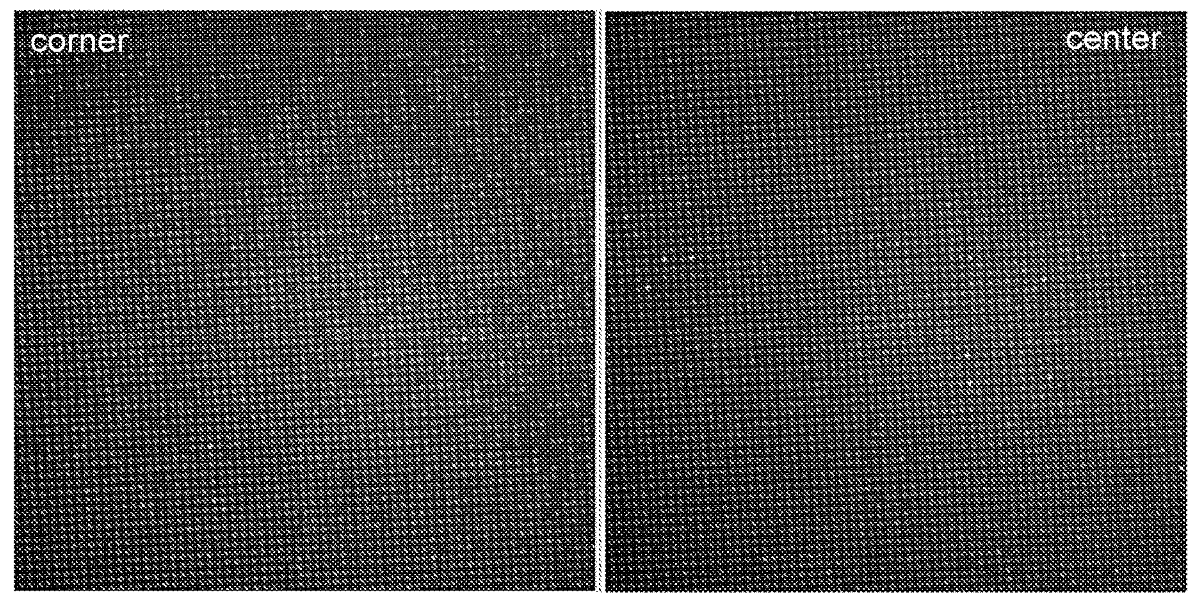
FIGS. 4A and 4B are images of the corner (FIG. 4A) and center (FIG. 4B) of a nanowell plate loaded with droplets comprising the detergent Tween 80.
Figures 5A, 5B:
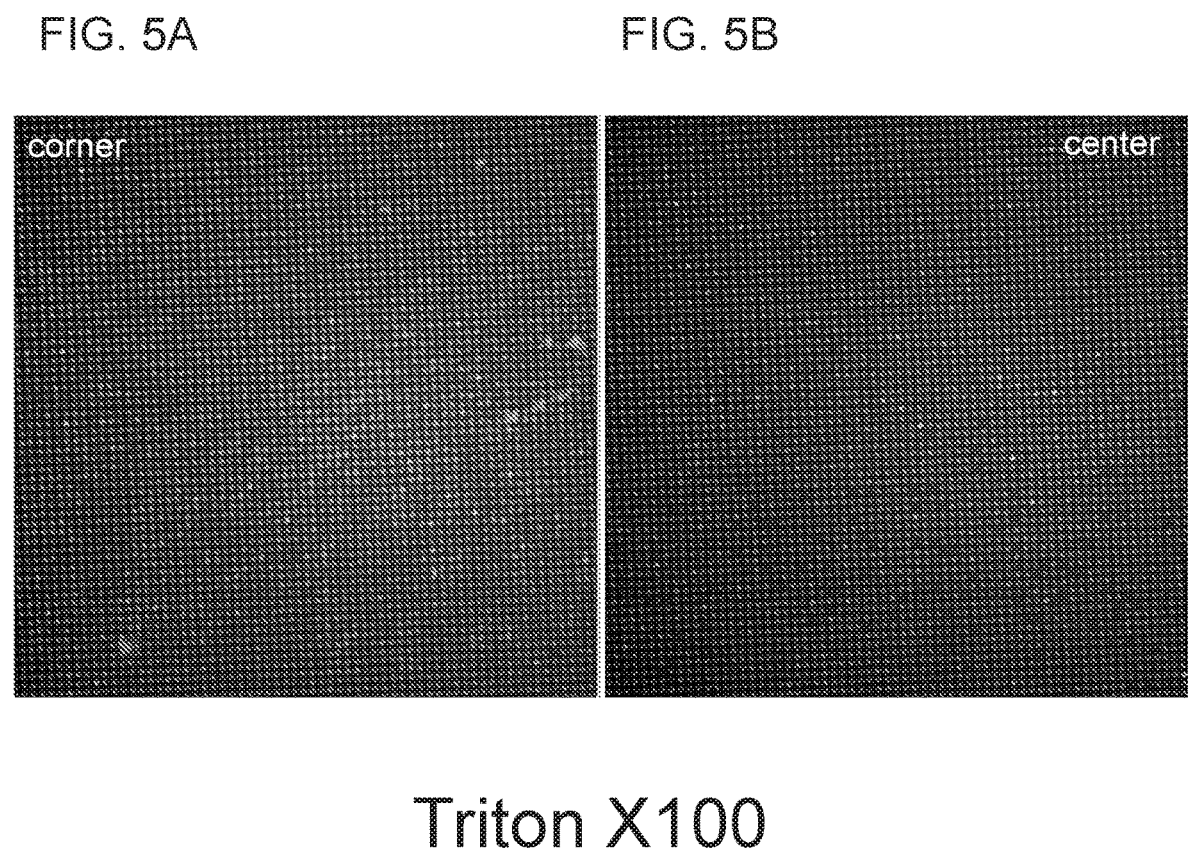

Indium tin oxide (ITO, 50 nm)-coated PET plastic (125 μm) nanowell arrays were tested using the following experimental conditions: 5 different detergents (Pluronic F68, Tetronic 90R4, Tween 20; Tween 80; Triton X 100); 0.05% in PBS; Tosyl beads (2.7 μm, functionalized with antibody); 20 seeding cycles; Plastic array; ROW 3.0-4.2; 30× magnification. The results for each detergent are shown in FIGS. 1-5. Tween 20, Tween 80, and Triton X 100 improved bead loading onto nanowell arrays.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of loading wells with liquid droplets, which method comprises:

(a) contacting an array of wells with a liquid droplet, wherein (i) one or more wells of the array is of sufficient size to have loaded therein a portion of the liquid droplet, and (ii) each portion of the liquid droplet comprises a solid support and a detergent or surfactant wherein the detergent is TWEEN-20 or TWEEN-80, and the surfactant is TRITON X-100, (b) moving the liquid droplet over the array of wells, wherein the detergent or surfactant reduces the contact angle between the liquid droplet and the wells, and whereby a portion of the liquid droplet is loaded into each well of the array;

(c) removing any portion of the liquid droplet that is not loaded into wells from the surface of the array; and (d) sealing the loaded wells.

2. The method of claim 1, wherein the wells are microwells or nanowells.

3. The method of claim 1, wherein the solid support is a bead.

4. The method of claim 3, wherein the bead is a microparticle.

5. The method of claim 1, wherein the solid support comprises an analyte of interest captured on the surface thereof.

6. The method of claim 1, wherein the liquid droplet is more efficiently loaded as compared to a liquid droplet that lacks a detergent or surfactant.

7. The method of claim 1, wherein moving the liquid droplet over the array of wells comprises applying an electric field across the array.

8. The method of claim 7, wherein applying an electric field comprises generating an alternating current.

9. The method of claim 1, wherein moving the liquid droplet over the array of wells comprises using a capillary element.

10. The method of claim 1, wherein the array of wells has a hydrophilic surface.

11. The method of claim 1, wherein the array of wells has a hydrophobic surface.

12. A method of detecting and quantifying an analyte of interest in a sample, which method comprises:

(a) providing a first liquid droplet containing an analyte of interest;

(b) providing a second liquid droplet containing a solid support which comprises a first binding member that specifically binds to the analyte of interest; wherein either the first liquid droplet or the second liquid droplet further comprises a detergent or surfactant;

(c) using energy to exert a force to manipulate the first liquid droplet and the second liquid droplet to create a droplet which comprises analyte of interest captured on the surface of the solid support;

(d) loading wells in an array with the liquid droplets according to any one of claims 1-11; and (e) detecting and quantifying the analyte of interest.

13. The method of claim 12, wherein detecting and quantifying the analyte of interest comprises adding a detectable label to the droplet before loading wells in an array with liquid droplets.

14. The method of claim 12, wherein detecting and quantifying the analyte of interest comprises adding a detectable label to the droplet after loading wells in an array with liquid droplets.

15. The method of claim 12, wherein the second liquid droplet comprises a detectable label.

16. The method of claim 13, wherein the detectable label comprises at least one second binding member that specifically binds to the analyte of interest.

17. The method of claim 16, wherein the detectable label comprises a chromagen, a fluorescent compound, an enzyme, a chemiluminescent compound, or a radioactive compound.

* * * * *